United States Patent [19]

Polito et al.

[11] Patent Number: 4,855,226

[45] Date of Patent: Aug. 8, 1989

[54] NOVEL COMPETITIVE ASSAY FOR THEOPHYLLINE AND REAGENT FOR USE THEREIN

[75] Inventors: Alan J. Polito, Danville; Anthony K. Cheng, Anaheim, both of Calif.

[73] Assignee: Beckman Instruments, Inc., Fullerton, Calif.

[21] Appl. No.: 742,264

[22] Filed: Jun. 7, 1985

[51] Int. Cl.$^4$ ............................................. G01N 33/53
[52] U.S. Cl. ........................................ 435/7; 436/537; 436/544; 436/545; 436/546; 436/801; 436/805; 436/808; 436/815; 530/807; 544/267; 544/268; 544/271; 544/272; 544/273
[58] Field of Search ............... 544/267, 268, 271, 272, 544/273; 435/7; 436/544, 545, 546, 801, 805, 808, 815, 909; 530/807

[56] References Cited

U.S. PATENT DOCUMENTS

| | | | |
|---|---|---|---|
| 4,156,081 | 5/1979 | Singh et al. | 435/7 |
| 4,297,494 | 10/1981 | Groman et al. | 544/267 |
| 4,302,438 | 11/1981 | Zech | 436/542 |
| 4,435,504 | 3/1984 | Zuk et al. | 436/530 |
| 4,510,251 | 4/1985 | Kirkemo et al. | 544/268 |
| 4,593,089 | 6/1986 | Wang et al. | 436/536 |

OTHER PUBLICATIONS

Chugai, Chemical Abstracts, 97:214131v, (1982).
Hackh's, Chemical Dictionary, 4th Edition, McGraw Hill Book Company, p. 35.
Nishikawa, Clinica Chemica Acta 91, pp. 59–65, (1979).

*Primary Examiner*—Robert J. Warden
*Assistant Examiner*—Robert Benson
*Attorney, Agent, or Firm*—W. H. May; Arnold Grant; Julia E. Abers

[57] ABSTRACT

A novel competitive assay for theophylline wherein caffeine-like (7-substituted) labeled conjugates are used to detect the presence and/or amount of theophylline present in a test sample. The use of such conjugates in a competitive assay for theophylline results in improved sensitivity of the assay method. Where the assay method is a nephelometric or turbidimetric inhibition immunoassay procedure, the assay was found to be less temperature dependent than prior art immunoassays.

14 Claims, No Drawings

NOVEL COMPETITIVE ASSAY FOR THEOPHYLLINE AND REAGENT FOR USE THEREIN

BACKGROUND OF THE INVENTION

1. Field of the Invention

This invention relates to xanthine derivatives and to nephelometric inhibition immunoassays and kits wherein they can be employed.

2. Description of the Prior Art

Nephelometry involves the detection of light scattered or reflected toward a detector that is not in the direct path of the transmitted light (1).

The basic principles governing nephelometric inhibition immunoassay (NIIA) were reported over 40 years ago by Pauling et al. (2,3) and examined again in detail by Pressman (4). These authors proved that one could quantify small amounts of hapten (molecules of less than 4000 $M_r$) by measuring chemically the decrease in the amount of precipitate formed from the interaction of hapten-specific antisera with polyhaptenic substances or conjugates of hapten with protein. The magnitude of the inhibition was best explained by the preferential interaction of the small quantity of hapten with antibodies of high avidity. The measurement of hapten by NIIA in which an endpoint nephelometer is used to measure the light scattered by reaction between a specific antibody and a hapten-macromolecular conjugate has been reported (5,6). Nishikawa et al. advanced the method into the area of therapeutic drug monitoring by describing similar endpoint NIIAs for phenytoin, phenobarbital, and theophylline (7,8).

Nephelometric procedures are a convenient tool for monitoring antigen-antibody reactions at an early stage, by detecting the growth of complexes ("scattering centers") capable of scattering light before they separate out of solution as immunoprecipitates. The formation of these scattering centers can be accelerated by the use of hydrophilic non-ionic polymers (e.g., dextran, polyethylene glycol), which increases the probability of protein-protein interaction by excluding a significant fraction of water. The use of polymers in an immunonephelometric assay also gives the advantages of increased sensitivity and less antiserum consumption (9).

The hapten of interest (a substance that can react with an antibody but cannot cause an immunological response) is covalently linked to a carrier protein, and the resulting conjugate is used to immunize animals. The specific antiserum is then reacted with a second conjugate or developer antigen, such that several hapten molecules are bound to each molecule of an unrelated carried protein. Therefore, although haptens cannot be quantitated by direct nephelometric procedures, by taking advantage of the fact that haptens will form soluble immune complexes, one can develop assays in which the hapten inhibits the formation of light-scattering centers produced by reacting a developer antigen with a limited amount of specific antibody.

Rate NIIAs have also been reported (10,11).

Nephelometric inhibition immunoassays as a whole also possess those advantages characteristic of all homogenous immunoassays (e.g., enzyme multiplied immunoassay and substrate-labeled fluorescence immunoassay), namely, increased accuracy and precision because of the elimination of a separation step (which is common to all heterogeneous immunoassays radioimmunoassays, enzyme-linked immunosorbent assay, etc.). In addition, NIIAs, which are readily adaptable to automation, involve extremely stable reagents, compared with assays that require radioactive or enzymelabeled tags, for which shelf life is a constant problem.

In the prior art there exists a nephelometric assay and kit for theophylline which employs a theophylline-8-butyric acid derivative having the following formula:

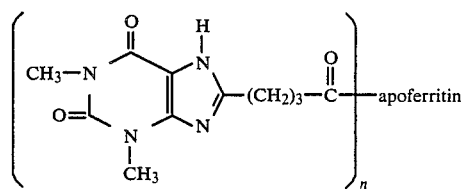

wherein n is the number of xanthine derivatives bonded to apoferritin. The cross-reactivity of the theophylline antiserum against major drugs and drug metabolites, i.e., the concentrations of cross-reactants in micrograms (μg) per milliliter (mL) required to produce a 30% error at a theophylline concentration of 10 μg/mL is set forth in Table I.

TABLE I
CROSS REACTIVITY OF THEOPHYLLINE ANTISERA

| Compound | Concentration μg/mL Producing a 30% Error at Theophylline 10 μg/mL |
| --- | --- |
| Caffeine | >200 |
| Theobromine | >100 |
| 1,7-Dimethylxanthine | >250 |
| 1-Methylxanthine | >100 |
| 3-Methylxanthine | >100 |
| 7-Methylxanthine | >100 |
| 1,3,7-Trimethyl Uric Acid | >250 |
| 1,3-Dimethyl Uric Acid | >40 |
| 1-Methyl Uric Acid | >200 |
| Uric Acid | >200 |
| 3-Methyl Uric Acid | >100 |
| Xanthine | >200 |
| Hypoxanthine | >100 |
| 8-Chlorotheophylline | >45 |
| Diphenhydramine | >200 |
| Diphylline | >100 |
| Aminophylline | >2.5 |

The correlation of this prior art theophylline assay kit with Syva Company's EMIT brand theophylline assay kit on a Gilford Instruments Model 203-S spectrophotometer is set forth in Table II.

TABLE II
COMPARISON OF PRIOR ART THEOPHYLLINE TEST AND REFERENCE METHOD

| Reference Method (X) | N | Least Squares Regression Equation | Correlation Coefficient |
| --- | --- | --- | --- |
| Syva/Gilford 203-S | 83 | y = 1.01X + 0.361 | 0.972 |

Although this prior art theophylline assay kit possesses a very low cross-reactivity and an excellent correlation with a reference method, it is very temperature sensitive. For example, the least square regression equations for observed (Y) versus expected (X) theophylline concentrations obtained at three different environmental (reaction) temperatures is set forth in Table III:

TABLE III

TEMPERATURE SENSITIVITY STUDY

| Temperature, °C. | Least Squares Regression Equation |
| --- | --- |
| 18 | Y = 1.7663X − 6.9895 |
| 25 | Y = 0.9211X + 1.1684 |
| 30 | Y = 0.8971X + 3.0655 |

Accordingly, it would be very desirable to have a NIIA and kit for use therein which also exhibits a low cross-reactivity and an excellent correlation with a reference method, but in addition thereto is less sensitive to environmental temperature changes.

SUMMARY OF THE INVENTION

In accordance with the present invention, there are provided an improved nephelometric inhibition immunoassay (NIIA) and a kit for use therein which exhibit low cross-reactivity and an excellent correlation with a reference method. In addition thereto, the NIIA and kit of the present invention exhibit a substantially lower dependence on environmental temperature changes. Because of such lower temperature dependence, the NIIA and kit of the present invention have improved precision and accuracy.

The improvement in the NIIA and kit is due to the use of a novel conjugate having a formula selected from a group consisting of

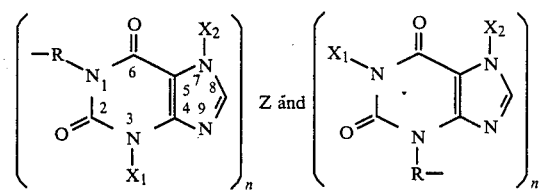

wherein:
(a) Z is a label;
(b) n is an integer of at least 1;
(c) R is a linking group; and
(d) $X_1$ and $X_2$ are independently selected from a group consisting of hydrocarbon and heterocarbon substituents containing from 1 to about 8 atoms other than hydrogen, said atoms being selected from a group consisting of carbon, oxygen, nitrogen, and sulfur.

The conjugate of the present invention, wherein Z is a poly(amino acid), also enables the NIIA and kit of the present invention to provide better sensitivity in the therapeutic range than the prior art NIIA and kit.

Also within the scope of this invention is a nephelometric inhibition assay of the type wherein a sample, which may have theophylline present therein, is contacted with a conjugate to form a solution. This solution is then contacted with a theophylline antibody to start a reaction in which the endogenous theophylline and the conjugate compete for the antibody. A function of any resulting conjugate-antibody complexation reaction is then measured. The NIIA of the present invention is characterized in that the above conjugate, wherein Z is a poly(amino acid), is employed therein.

The present invention also encompasses a kit. The kit is of the type which comprises a first unit comprising a conjugate and a second unit which comprises theophylline antibody. The kit is characterized in that the above conjugate is employed therein.

Still other features and attendant advantages of the present invention will become apparent to those skilled in the art from a reading of the following detailed description of the preferred embodiments.

DESCRIPTION OF THE PREFERRED EMBODIMENTS

Preferably, the label Z is selected from a group consisting of fluorescent, bioluminescent, chemiluminescent, and radioactive labels and poly(amino acids) having a molecular weight of at least about 3,000. Usually, the poly(amino acid) is selected from a group consisting of polypeptides, proteins, antigens, and enzymes having a molecular weight of from about 3,000 to about 10,000,000. More preferably, the poly(amino acid) is as shown in Table IV.

TABLE IV

| Type of poly(amino acid) | molecular weight | n | |
| --- | --- | --- | --- |
| polypeptides, proteins, or antigens | 3,000–10,000,000 | 1–250 | ↓ Increasing |
| | 10,000–1,000,000 | 2–150 | ↓ preference |
| | 25,000–800,000 | 4–100 | ↓ |
| enzymes | 10,000–600,000 | 1–30 | ↓ Increasing |
| | 10,000–150,000 | 2–20 | ↓ preference |
| | 12,000–80,000 | 2–12 | ↓ |

When Z is a poly(amino acid), n is preferably from about 1 to about 250. Further preferred embodiments of n are set forth in Table IV.

When Z is either a fluorescent, bioluminescent, chemiluminescent, or radioactive label, n is 1.

Preferably, R is selected from the group consisting of from 1 to about 12 atoms other than hydrogen, such atoms being selected from the groups consisting of carbon, oxygen, nitrogen, and sulfur. More preferably, R has a formula

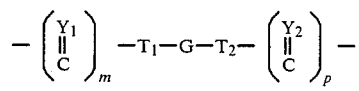

wherein:
$Y_1$ and $Y_2$ are independently selected from a group consisting of oxygen, imino, and sulfur;
$T_1$ is a hydrocarbon radical containing from 1 to about 10 carbon atoms;
$T_2$ is selected from a group consisting of hydrocarbon and hydrocarbylamino radicals containing from about 1 to about 10 carbon atoms, provided that when $T_2$ is hydrocarbylamino, the nitrogen is bonded to $(CY_2)$;
G is selected from a group consisting of a bond, amido, and oxy;
m is zero or 1;
p is zero or 1; and
$(CY_1)$ is bonded to $N^1$ or $N^3$ and $(CY_2)$ is bonded to the poly(amino acid). Optimally, R has a formula

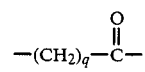

wherein:
q is an integer from 1 to about 8, more preferably from about 2 to about 6; and
(CO) is bonded to the poly(amino acid).

Preferably, $X_1$ and $X_2$ are independently selected from the group consisting of hydrocarbon substituents. It is further preferred that the hydrocarbon substituents contain from 1 to about 6, more preferably 1 to about 4, and optimally 1 to about 2 carbon atoms.

In one particularly preferred embodiment, the poly(amino acid) is apoferritin; $X_1$ and $X_2$ are both methyl groups; R is $-(CH_2)_4-(CO)-$, wherein (CO) is bonded to apoferritin; and n is an integer from about 6 to about 60.

The conjugates of the present invention can be synthesized via any applicable procedure known to those skilled in the art.

The conjugates of the present invention wherein Z is a poly(amino acid) can be employed in any known nephelometric methodology. In a nephelometric methodology it is necessary to measure a function of any resulting conjugate-antibody complexation reaction. In the case of an end-point assay, the function to be measured is the intensity of scattered light. In a rate assay, the function to be measured is the rate of change of the intensity of the scattered light.

In an NIIA rate assay, it is also preferred that a trigger be incorporated into either the first or second units of the kit. Such a trigger is well known to those skilled in the art and is described in U.S. Pat. No. 4,157,871 (11). In this preferred aspect of the invention, either the first solution, which comprises endogenous theophylline and a conjugate within the scope of this invention, will further have a trigger present therein or a first solution devoid of such trigger will be simultaneously contacted with theophylline antibody and the trigger.

When Z is selected from a group consisting of enzyme, fluorescent, bioluminescent, chemiluminescent, and radioactive labels, the conjugates of the present invention can be employed in enzyme, fluorescent, bioluminescent, chemiluminescent, and radio immunoassays, respectively.

The following examples are provided for the purpose of further illustration and are not intended to be limitations on the disclosed invention.

EXAMPLE 1

The cross-reactivity of a theophylline antiserum against major drugs and drug metabolites in an NIIA assay employing conjugates of the following formulas is set forth in Table V.

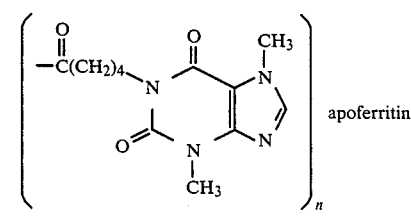

1-(5'-carboxybutyl)theobromineapoferritin conjugate and

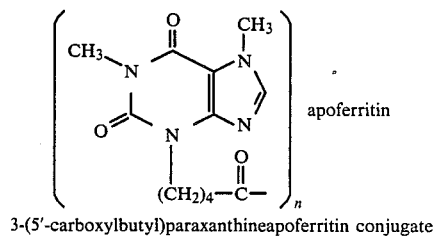

3-(5'-carboxylbutyl)paraxanthineapoferritin conjugate

TABLE V

| | Cross-Reactivities | |
|---|---|---|
| | Concentration μg/mL Producing a 30% Error at Theophylline 10 μg/mL | |
| Compound | Paraxanthine 3-apoferritin Conjugate | Theobromine-1-apoferritin Conjugate |
| Caffeine | 60 | ≧75 |
| Theobromine | 80 | ≧80 |
| 1,7-dimethylxanthine | 80 | ≧80 |
| 1-methylxanthine | >100 | ≧100 |
| 3-methylxanthine | >100 | ≧100 |
| 7-methylxanthine | >100 | ≧100 |
| 1,3,7-trimethyl uric acid | >250 | >250 |
| 1,3-dimethyl uric acid | ≧10 | ≧10 |
| 1-methyl uric acid | >105* | ≧200 |
| Uric acid | >105* | ≧200 |
| 3-methyl uric acid | 100 | ≧200 |
| Xanthine | >105* | ≧200 |
| Hypoxanthine | >100 | ≧200 |
| 8-chlorotheophylline | ≧20 | ≧17 |
| Diphenhydramine | >100 | ≧200 |
| Dyphylline | >100 | ≧100 |
| Aminophylline | >2.5* | ≧25 |

*Highest concentration tested

Although the extent of cross-reactivity is somewhat increased with the conjugates within the scope of this invention, the extent of cross-reactivity is still better than or equal to the cross-reactivity claimed by various commercial kits. Further, although the conjugates within the scope of this invention exhibited an increase in cross-reactivity with 1,3-dimethyl uric acid, such increase is not of conern because it is believed that this compound will not be found in serum in concentrations which will effect theophylline values reported.

EXAMPLE 2

The correlation of a theophylline assay kit employing the theobromine conjugate was made with Syva Company's EMIT brand theophylline assay kit run on a Gilford instrument Model 203-S spectrophotometer. The results from this study is set forth in Table VI.

TABLE VI

| Composition Within Scope of Present Invention and Reference Methods of a Theophylline Test | | | |
|---|---|---|---|
| Reference Method (X) | N | Least Squares Regression Equation | Correlation Coefficient |
| Syva/Gilford 203-S | 61 | y = 1.00X + 0.14 | 0.989 |

Table VI indicates that a theophylline assay kit within the scope of the present invention also has an excellent correlation with a reference method.

EXAMPLE 3

Temperature studies were performed to determine the extent to which values would be affected by environmental temperature changes. For each temperature indicated, a linearity run was performed on two different manual Beckman Instruments brand ICS II nephelometric instruments located in a temperature-controlled environmental chamber. The least square regression equations for observed (Y) versus expected (X) theophylline concentrations obtained at three different environmental temperatures is set forth in Table VII.

TABLE VII

Temperature Sensitivity Study

| Temperature, °C. | Least Squares Regression Equation |
|---|---|
| 18 | Y = 1.0829 X −0.8454 |
| 25 | Y = 1.0397 X −0.7916 |
| 30 | Y = 0.9581 X −0.2882 |

As can be seen from the least square regression equations set forth in Table VII, a theophylline assay and kit within the scope of this invention is much less sensitive to environmental temperature changes.

Based on this disclosure, many other modifications and ramifications will naturally suggest themselves to those skilled in the art. These are intended to be within the scope of this invention.

BIBLIOGRAPHY

1. Kusnetz et al., Automated Immunoanalysis, 1, R.F. Ritchie, Ed., Marcel Dekker, Inc., New York, N.Y. (1978) pp. 1-42.
2. Pauling, et al., J. Am. Chem. Soc., 64:2994-3003 (1942).
3. Pauling et al., J. Am. Chem. Soc., 64:3003-3009 (1942).
4. Pressman, Methods Med. Res., 10:122-127 (1964).
5. Cambiaso et al., J. Immunol. Methods, 5:293-302 (1974).
6. Gauldie et al., Automated Immunoanalysis, 1, R.F. Ritchie, Ed., Marcel Dekker, Inc., New York, N.Y. 1978) pp. 321-333.
7. Nishikawa et al., J. Immunol. Methods, 29:85-89 (1979).
8. Nishikawa et al., Clin. Chem. Acta, 91:59-65 (1979).
9. Hellsing, Protides Biol. Fluids, 21, H. Peters, Ed., Pergamom, Oxford (1974) pp. 579-583.
10. Anderson et al., Automated Immunoanalysis, 2, R.F. Ritchie, Ed., Marcel Dekker, Inc., New York, N.Y. (1978) pp. 409-469.
11. U.S. Pat. No. 4,157,871.

The embodiments of the invention in which an exclusive property or privilege is claimed are defined as follows:

1. A competitive immunoassay method for detecting theophylline which may be present in a test sample comprising:
   (a) contacting said test sample with antitheophylline antibody and a labelled conjugate having a formula selected from the group consisting of

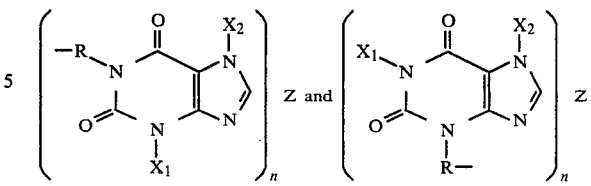

wherein:
   (1) Z is a label;
   (2) n is an integer of at least 1;
   (3) R is a linking group;
   (4) $X_1$ is a methyl group; and
   (5) $X_2$ is a hydrocarbon chain of up to 6 carbon atoms and,
   (b) detecting the presence and/or amount of labelled conjugate complexed with said antitheophylline antibody 2. The method of claim 1 wherein said label is selected from the group consisting of fluorescent, bioluminescent, chemiluminescent, radioactive, and protein labels.
3. The method of claim 2 wherein said label is a protein.
4. The method of claim 3 wherein said method is a nephelometric or turbidimetric inhibition immunoassay.
5. The method of claim 1 wherein $X_2$ is a methyl group.
6. The method of claim 5 wherein said label is selected from the group consisting of fluorescent, bioluminescent, chemiluminescent, radioactive, and protein labels.
7. The method of claim 6 wherein said label is a protein.
8. The method of claim 7 wherein said method is a nephelometric or turbidimetric inhibition immunoassay.
9. A reagent for use in a competitive immunoassay method for detecting theophylline comprising antitheophylline antibody and a labelled conjugate having a formula selected from the group consisting of

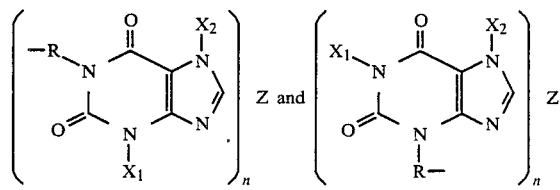

wherein:
   (1) Z is a label;
   (2) n is an integer of at least 1;
   (3) R is a linking group;
   (4) $X_1$ is a methyl group; and
   (5) $X_2$ is a hydrocarbon chain of up to 6 carbon atoms.

10. The reagent of claim 9 wherein said label is selected from the group consisting of fluorescent, bioluminescent, chemiluminescent, radioactive, and protein labels.
11. The reagent of claim 10 wherein said label is a protein.
12. The reagent of claim 11 wherein $X_2$ is a methyl group.
13. The reagent of claim 12 wherein said label is selected from the group consisting of fluorescent, bioluminescent, chemiluminescent, radioactive and protein labels.
14. The reagent of claim 13 wherein said label is a protein.

* * * * *